(12) United States Patent
Inoue et al.

(10) Patent No.: US 9,841,385 B2
(45) Date of Patent: Dec. 12, 2017

(54) PATTERN CHARACTERISTIC-DETECTION APPARATUS FOR PHOTOMASK AND PATTERN CHARACTERISTIC-DETECTION METHOD FOR PHOTOMASK

(75) Inventors: Hiromu Inoue, Kanagawa-ken (JP); Hiroyuki Ikeda, Kanagawa-ken (JP); Eiji Sawa, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 464 days.

(21) Appl. No.: 12/857,906

(22) Filed: Aug. 17, 2010

(65) Prior Publication Data

US 2011/0058729 A1  Mar. 10, 2011

(30) Foreign Application Priority Data

Sep. 9, 2009 (JP) .................................. 2009-208310

(51) Int. Cl.
*G03F 1/84* (2012.01)
*G01N 21/956* (2006.01)
*G03F 7/20* (2006.01)

(52) U.S. Cl.
CPC .............. *G01N 21/956* (2013.01); *G03F 1/84* (2013.01); *G03F 7/7065* (2013.01); *G03F 7/70525* (2013.01); *G03F 7/70625* (2013.01)

(58) Field of Classification Search
CPC combination set(s) only.
See application file for complete search history.

(56) References Cited

U.S. PATENT DOCUMENTS 5,365,251 A * 11/1994 Denber .................. G06K 15/02
  345/611
6,304,623 B1 * 10/2001 Richards .................. H03L 7/18
  375/355

(Continued)

FOREIGN PATENT DOCUMENTS

JP  7-128248  5/1995
JP  11-304719  11/1999

(Continued)

OTHER PUBLICATIONS

Office Action dated Jul. 28, 2011 in Korea Application No. 10-2010-0084429 (With English Translation).

(Continued)

*Primary Examiner* — Luna Champagne
(74) *Attorney, Agent, or Firm* — Oblon, McClelland, Maier & Neustadt, L.L.P.

(57) ABSTRACT

According to one embodiment, a pattern characteristic detection apparatus for a photomask includes a detection-data creating portion, a reference-data creating portion, an extracting portion, a first area-setting portion, a detecting portion and an collecting portion. The detection-data creating portion is configured to create detection data on the basis of an optical image of a pattern formed on a photomask. The reference-data creating portion is configured to create reference data of the pattern. The extracting portion is configured to extract a pattern for pattern characteristic detection and positional information of the extracted pattern. The first area-setting portion is configured to set an area where pattern characteristics are to be detected, and configured to extract a target pattern. The detecting portion is configured to detect pattern characteristics of the target pattern within the area. In addition, the collecting portion is configured to collect the detected pattern characteristics.

5 Claims, 6 Drawing Sheets

(56) References Cited

U.S. PATENT DOCUMENTS

| | | | |
|---|---|---|---|
| 6,829,465 B2* | 12/2004 | Yamanaka et al. | 399/301 |
| 6,856,931 B2* | 2/2005 | Yoshida | 702/127 |
| 6,856,932 B1* | 2/2005 | Wallace | 702/130 |
| 7,133,549 B2 | 11/2006 | Eran et al. | |
| 7,260,266 B2* | 8/2007 | Nakajima et al. | 382/240 |
| 7,953,269 B2* | 5/2011 | Kudou | 382/141 |
| 2009/0303323 A1 | 12/2009 | Yoshikawa et al. | |

FOREIGN PATENT DOCUMENTS

| | | |
|---|---|---|
| JP | 2002-328462 | 11/2002 |
| JP | 2005-196471 | 7/2005 |
| JP | 2005-300884 | 10/2005 |
| JP | 2007-192743 | 8/2007 |
| KR | 10-1999-0083456 | 11/1999 |

OTHER PUBLICATIONS

Amir Sagiv et al., "IntenCD™: Mask Critical Dimension Variation Mapping", SPIE, vol. 7028, 2008, 12 pages.
Carl Hess et al., "High Resolution Inspection with Wafer Plane Die: Database Defect Detection", SPIE, vol. 7122, 2008, 11 pages.

\* cited by examiner

PATTERN CHARACTERISTIC-DETECTION APPARATUS FOR PHOTOMASK AND PATTERN CHARACTERISTIC-DETECTION METHOD FOR PHOTOMASK

CROSS-REFERENCE TO RELATED APPLICATIONS

This application is based upon and claims the benefit of priority from the prior Japanese Patent Application No. 2009-208310, filed on Sep. 9, 2009; the entire contents of which are incorporated herein by reference.

FIELD

Embodiments described herein relate generally to a characteristic-detection apparatus for a photomask and a characteristic-detection method for a photomask.

BACKGROUND

In the fields of semiconductor devices, flat-panel displays, micro electro mechanical systems (MEMS), circuit boards, optical devices, mechanical devices, and the like, various structures with patterns formed on their surfaces are fabricated. In the manufacturing of such structures, various kinds of testing are performed to find whether or not there are any defects such as defective shapes of patterns, defective dimensions of patterns, and existence of foreign objects.

A testing method called the die-to-database method is known as a method of finding defects of patterns formed on surfaces of structures. According to this testing method, defects are detected by comparing test data with reference data. To obtain the test data, an enlarged optical image of a pattern is formed on the light-receiving surface of a charge coupled device (CCD) image sensor or the like. The reference data, on the other hand, are obtained on the basis of the design data (CAD data) used to design the pattern or the like. If there is a difference between the test data and the reference data, then the difference is detected as a defect.

A known pattern-testing apparatus detects defects such as wrong sizes and wrong positions of contact-hole patterns, which are microscopic patterns, on the basis of the sum of the luminance values of the light that passes through an area to be tested (for example, refer to JP-A 7-128248 (1995) (Kokai)).

A photomask testing apparatus to be used in manufacturing semiconductor devices checks whether or not there is any defect, and also sometimes detects line widths of the microscopic line-and-space patterns.

In addition, there is known an apparatus for evaluating the printability of photomask pattern that are printed to the surfaces of wafers by an exposure device. The apparatus picks up an enlarged optical image of the pattern of a photomask by a CCD sensor or the like, using an optical system equivalent to that of the exposure device, and thus detects the transmittance magnitude or the line widths of the calculated wafer plane pattern.

The apparatus capable of evaluating the printablity, however, employs a technique with a limited capability of detecting: the transmittance of contact-hole patterns; and the line widths of the line-and-space patterns. Specifically, the technique only enables detection within a limited area. That is, the apparatus can perform detection at predetermined intervals, but cannot perform detection with high resolution on all over the area of the photomask. On the other hand, some of the apparatuses to test photomasks have functions to acquire the distribution of line widths, but still are not capable of acquiring the line-width distribution with the printablity taken into consideration. Accordingly, characteristics or characteristic profiles of the photomasks (such as, the transmittance profile, the line widths profile with the printablity taken into consideration) cannot be detected from all over the area of the photomask with high resolution.

The patterns on photomasks have been more and more microscopic in recent years. In such circumstances, there is a growing demand to improve detection sensitivity of contact-hole patterns, and to precisely evaluate the quality of photomasks, the cause of the lowering of the process margin attributable to the photomasks, and the like.

The conventional technique to detect the transmittance or line widths, however, is not capable of detecting the characteristics or the characteristic distributions of photomasks. Accordingly, when the process margin or the yield is lowered due to an anomaly not so serious as to be regarded as a defect, the cause of the lowering may not be identified, for example.

DETAILED DESCRIPTION OF THE INVENTION

In general, according to one embodiment, a pattern characteristic detection apparatus for a photomask includes a detection-data creating portion, a reference-data creating portion, an extracting portion, a first area-setting portion, a detecting portion and an collecting portion. The detection-data creating portion is configured to create detection data on the basis of an optical image of a pattern formed on a photomask. The reference-data creating portion is configured to create reference data of the pattern. The extracting portion is configured to extract, from the reference data, a pattern for pattern characteristic detection and positional information of the extracted pattern. The first area-setting portion is configured to set an area where pattern characteristics are to be detected on the basis of the extracted pattern, and configured to extract, from the detection data, a target pattern for the pattern characteristic detection on the basis of the positional information of the extracted pattern. The detecting portion is configured to detect pattern characteristics of the target pattern for the pattern characteristic detection within the area where the pattern characteristics are to be detected by converting light intensity of an optical image formed on a CCD image sensor into electric digital signal. In addition, the collecting portion is configured to collect the detected pattern characteristics.

According to another embodiment, a pattern characteristic detection apparatus for a photomask includes a detection-data creating portion, a reference-data creating portion, an extracting portion, an inversely-transforming portion, an inverse-transforming portion, a wafer plane pattern computing portion, a second area-setting portion, a detecting portion and an collecting portion. The detection-data creating portion is configured to create detection data on the basis of an optical image of a pattern formed on a photomask. The reference-data creating portion is configured to create reference data of the pattern. The extracting portion is configured to extract, from the reference data, a pattern for pattern characteristic detection and positional information of the extracted pattern. The inverse-transforming portion is configured to perform an inverse-transformation operation to calculate, from the detection data of a pattern formed on a photomask. The wafer plane pattern computing portion is configured to calculate a wafer plane pattern from the pattern formed on the photomask. The second area-setting portion is configured to set an area where pattern characteristics are to be detected on the basis of the extracted pattern, and configured to extract, from the wafer plane pattern, a target pattern for the pattern characteristic detection on the basis of the positional information of the extracted pattern. The detecting portion is configured to detect pattern characteristics of the target pattern for the pattern characteristic detection within the area where the pattern characteristics are to be detected. In addition, the collecting portion is configured to collect the detected pattern characteristics.

According to another embodiment, a pattern characteristic detection apparatus for a photomask includes a detection-data creating portion, a reference-data creating portion, an extracting portion, a transforming portion, a wafer plane pattern computing portion, a second area-setting portion, a detecting portion and a collecting portion. The detection-data creating portion is configured to create detection data on the basis of an optical image of a pattern formed on a photomask. The reference-data creating portion is configured to create reference data of the pattern. The extracting portion is configured to extract, from the reference data a pattern for pattern characteristic detection and positional information of the extracted pattern. The transforming portion is configured to calculate the pattern formed on a photomask from the detection data by calculating a pattern that correlates most with the detection data by a correlation operation. The wafer plane pattern computing portion is configured to calculate a wafer plane pattern from the pattern formed on the photomask. The second area-setting portion is configured to set an area where pattern characteristics are to be detected on the basis of the extracted pattern, and configured to extract, from the wafer plane pattern a target pattern for the pattern characteristic detection on the basis of the positional information of the extracted pattern. The detecting portion is configured to detect pattern characteristics of the target pattern for the characteristic detection within the area where the pattern characteristics are to be detected. In addition, the collecting portion is configured to collect the detected pattern characteristics.

According to another embodiment, a method of detecting pattern characteristics of a photomask is disclosed. The method includes creating detection data on the basis of an optical image of a pattern formed on a photomask and creating reference data of the pattern. The method includes extracting, from the reference data, a pattern for pattern characteristic detection and positional information of the extracted pattern. The method includes setting an area where pattern characteristics are to be detected on the basis of the extracted pattern, and extracting, from the detection data, the target pattern for the pattern characteristic detection on the basis of the positional information of the extracted pattern. The method includes detecting pattern characteristics of the target pattern for the pattern characteristic detection within the area where the pattern characteristics are to be detected. In addition, the method includes collecting the detected pattern characteristics.

According to another embodiment, a method of detecting pattern characteristics of a photomask is disclosed. The method includes creating detection data on the basis of an optical image of a pattern formed on a photomask and creating reference data of the pattern. The method includes extracting, from the reference data, a pattern for pattern characteristic detection and positional information of the extracted pattern. The method includes performing an inverse-transformation operation to calculate, from the detection data, a pattern formed on a photomask. The method includes calculating a wafer plane pattern from the pattern formed on the photomask. The method includes setting an area where pattern characteristics are to be detected on the basis of the extracted pattern, and extracting, from the wafer plane pattern, the target pattern for the characteristic detection on the basis of the positional information of the extracted pattern. The method includes detecting pattern characteristics of the target pattern for the characteristic detection within the area where the pattern characteristics are to be detected. In addition, the method includes collecting the detected pattern characteristics.

Some embodiments will be described below by referring to the drawings. Note that, in the following drawings, the same or similar reference numerals denote the same or similar constituent elements, and detailed description thereof is omitted appropriately.

Figure 1:
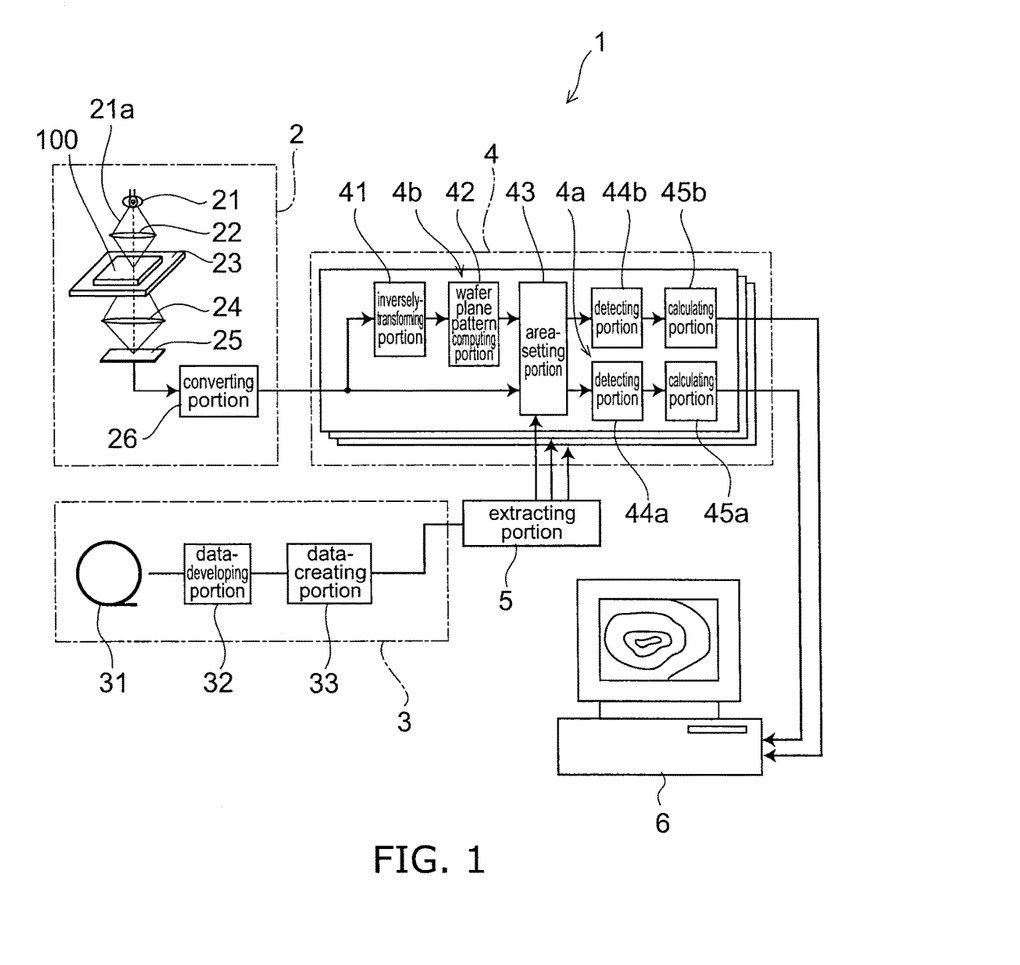
FIG. 1 is a block diagram for illustrating a characteristic-detection apparatus for a photomask according to this embodiment.

FIG. 1 is a block diagram for illustrating a characteristic-detection apparatus for photomasks according to this embodiment.

FIG. 1 shows a characteristic-detection apparatus 1, which includes a detection-data creating portion 2, a reference-data creating portion 3, a characteristic-detecting portion 4, an extracting portion 5, and a displaying portion 6.

The detection-data creating portion 2 includes a light source 21, an illuminating optical system 22, a mounting portion 23, an imaging optical system 24, a detecting portion 25, and a converting portion 26.

The detection-data creating portion 2 creates detection data based on an optical image of a pattern formed on a test sample 100 (e.g., photomask).

The light source 21 emits detecting light 21a. Various kinds of light sources—e.g., light sources that emit white light, monochromatic lights, coherent light, or the like—can be used as the light source 21. A preferable light source used as the light source 21 to perform detection on a microscopic pattern is one that is capable of emitting detecting light 21a with short wavelengths. An example of such light sources is YAG-laser light source that emits detecting light 21a with a wavelength of 266 nm. Note that the light source 21 is not limited to a laser light source. Light sources of other kinds may be selected appropriately for the size of the pattern, or other determining factors.

The illuminating optical system 22 guides the detecting light 21a emitting from the light source 21. The detecting light 21a thus guided is cast onto the detection area on the test sample 100. In addition, the illuminating optical system 22 controls the size of the portion illuminated by the detecting light 21a.

The imaging optical system 24 guides the detecting light 21a coming from the test sample 100. The detecting light 21a thus guided is cast onto the light-receiving surface of the detecting portion 25, and form an image on the light-receiving surface.

Each of the illuminating optical system 22 and the imaging optical system 24 has such a configuration as one shown in FIG. 1. The configuration includes various optical elements, such as a lens. The kinds of and the positions of the optical elements shown in FIG. 1 are not the only possible ones, and may be changed appropriately. Each of the illuminating optical system 22 and the imaging optical system 24 may include optical elements other than the ones shown in FIG. 1 if necessary. Some of the possible additional optical elements are a mirror, a diaphragm, a beam splitter, a magnifying-power changer, and a zooming mechanism.

The imaging optical system 24 shown in FIG. 1 is one that guides the detecting light 21a, passing through the test sample 100, to the detecting portion 25. The imaging optical system 24, however, may be configured to guide the detecting light 21a, reflected by the test sample 100, to the detecting portion 25.

The mounting portion 23 holds the test sample 100, mounted on the 23. The mounting portion 23 is equipped with an unillustrated unit for moving the test sample 100, mounted on the mounting portion 23, from one position to another so that the position to be actually subjected to the detection can be changed accordingly. The unillustrated unit for moving the test sample 100 is not necessarily provided in the mounting portion 23. All that is necessary is a unit for changing the relative position to be actually subjected to the detection. A possible solution is providing an unillustrated unit for moving and changing the positions of the illuminating optical system 22, the imaging optical system 24, the detecting portion 25, and the like.

The detecting portion 25 converts the light of the optical image, formed on the light-receiving surface, into electricity. For instance, a charge coupled device (CCD) sensor, a CCD line sensor, a time delay and integration (TDI) sensor, or the like can be used as the detecting portion 25. However, the detecting portion 25 is not limited to these sensors. A sensor that is capable of converting the light of the formed optical image into electricity may be selected appropriately.

The converting portion 26 converts the analogue electric signal outputted from the detecting portion 25 into a digital signal. The converting portion 26 then graphically interprets the resultant digital electric signal to create detection data.

The reference-data creating portion 3 includes a data-storing portion 31, a data-developing portion 32, and a data-creating portion 33.

The reference-data creating portion 3 creates reference data based on the design data or the like stored in the data-storing portion 31. The reference data thus created by the reference-data creating portion 3 are on the pattern formed on the photomask.

The data-storing portion 31 stores such data as drawing data to be used for forming the pattern, or designed data that have not been transformed into drawing data yet.

The data-developing portion 32 develops the design data or the like acquired from the data-storing portion 31, and thus creates two-dimensional data.

The data-creating portion 33 creates reference data by graphically interpreting the resultant two-dimensional data. The reference data are created to be suitable for the resolution of the detection data. Specifically, the data-creating portion 33 transforms the data having been developed by the data-developing portion 32 into reference data with a resolution that is approximately as high as the resolution of the data (i.e., the detection data) on the optical image acquired by the detecting portion 25.

The extracting portion 5 extracts, from the reference data, a pattern with the same shape and size as those of the target pattern for the detection of characteristics (e.g., transmittance or the like). The extracting portion 5 outputs, to an area-setting portion 43, a signal (i.e., valid flag) about the extracted pattern (i.e., reference pattern). When outputting the above-mentioned signal, the extracting portion 5 also outputs the positional information of the extracted pattern (i.e., reference pattern), that is, the information on where in the photomask the extracted pattern (i.e., reference pattern) is situated.

In short, the extracting portion 5 extracts, from the reference data, both the reference pattern corresponding to the target pattern for the characteristic detection and the positional information of the extracted pattern (the reference pattern). The extracting portion 5 then outputs, to the area-setting portion 43, both the signal (valid flag) about the extracted reference pattern and the positional information of the reference pattern. More details about the extracting portion 5 will be given later.

The characteristic-detecting portion 4 includes a first characteristic-detecting portion 4a and a second characteristic-detecting portion 4b. Plural characteristic-detection portions each of which is provided with the first characteristic-detecting portion 4a and the second characteristic-detecting portion 4b may be provided.

The first characteristic-detecting portion 4a detects characteristics (e.g., transmittance or the like) of the pattern of the detection data corresponding to the reference pattern extracted by the extracting portion 5. In addition, the first characteristic-detecting portion 4a performs collection, or the like, of the characteristics thus detected.

The first characteristic-detecting portion 4a includes the area-setting portion 43, a detecting portion 44a, and a collecting portion 45a.

On the basis of the signal (i.e., valid flag) received from the extracting portion 5, the area-setting portion 43 sets an area as the target area where the characteristics (e.g., transmittance or the like) of the pattern are to be detected. In addition, on the basis of the positional information received also from the extracting portion 5, the area-setting portion 43 extracts, from the detection data, the target pattern for the characteristic detection. To put it differently, on the bases of the reference pattern, the area-setting portion 43 determines the area where the characteristics are to be detected. In addition, also on the basis of the positional information, the area-setting portion 43 extracts, from the detection data, the target pattern for the characteristic detection.

On the basis of the area set as the target area for the characteristic detection by the area-setting portion 43 and the target pattern for the characteristic detection, the detecting portion 44a detects characteristics of the pattern. To put it differently, the detecting portion 44a detects the characteristics of the target pattern for the characteristic detection situated in the target area for the characteristic detection.

The collecting portion 45a performs a calculation on the characteristics detected by the detecting portion 44a. The collecting portion 45a may be configured to calculate the characteristics for the entire area of the photomask on the basis of the detected characteristics. In addition, the collecting portion 45a may be configured to create information on characteristic profiles (e.g., transmittance profile or the like) on the basis of the detected characteristics and the positional information.

The second characteristic-detecting portion 4b performs an inverse-transformation operation to calculate, from the detection data, the pattern formed on the photomask. Subsequently, on the basis of the calculated pattern formed on the photomask, the second characteristic-detecting portion 4b calculates, by a simulation, the pattern (wafer plane pattern) to be transferred onto the surface of the test sample 100. The second characteristic-detecting portion 4b then detects the characteristics (e.g., transmittance or the like) of the wafer plane pattern corresponding to a specific position in the reference pattern, and then performs collection or the like on the detected characteristics. Details of the inverse-transformation operation and of the operation using the wafer plane pattern will be described later.

The second characteristic-detecting portion 4b includes an inversely-transforming portion 41, a wafer plane pattern computing portion 42, the area-setting portion 43, a detecting portion 44b, and a calculating portion 45b.

The inversely-transforming portion 41 performs an inverse-transformation operation to calculate, from the detection data, the pattern formed on the photomask. The inverse-transformation operation uses the optically-imaging characteristics of the imaging optical system 24—i.e., the point spread function (PSF) of the imaging optical system 24—and the image-forming function representing the sensitivity profile of the pixels included in the detecting portion 25.

The wafer plane pattern computing portion 42 calculates the wafer plane pattern from the pattern formed on the photomask and calculated by the inversely-transforming portion 41.

On the basis of the signal (i.e., valid flag) received from the extracting portion 5, the area-setting portion 43 sets an area as the area where the characteristics (e.g., transmittance or the like) of the pattern are to be detected. In addition, on the basis of the positional information received also from the extracting portion 5, the area-setting portion 43 extracts, from the wafer plane pattern calculated by the wafer plane pattern computing portion 42, the target pattern for the characteristic detection. To put it differently, on the bases of the reference pattern, the area-setting portion 43 determines the area where the characteristics are to be detected. In addition, also on the basis of the positional information, the area-setting portion 43 extracts, from the wafer plane pattern, the target pattern for the characteristic detection.

On the basis of the area for the characteristic detection set as the target area by the area-setting portion 43 and the target pattern for the characteristic detection, the detecting portion 44b detects characteristics of the pattern. To put it differently, the detecting portion 44b detects the characteristics of the target pattern for the characteristic detection situated in the target area for the characteristic detection.

The collecting portion 45b performs a calculation on the characteristics detected by the detecting portion 44b. The collecting portion 45b may be configured to calculate the characteristics for the entire area of the photomask on the basis of the detected characteristics. In addition, the collecting portion 45b may be configured to create information on characteristic profiles (e.g., transmittance profile or the like), on the basis of the detected characteristics and the positional information.

More detailed descriptions will be given later of how to determine the target area for the characteristic detection, how to perform the characteristic detection, and how to perform the calculation or the like of the characteristics.

The displaying portion 6 provides visual presentations based on the data on the characteristics calculated by the calculating portions 45a and 45b. For instance, the displaying portion 6 may displays a chart of the characteristic profiles (e.g., a chart of transmittance profile or the like). As described earlier, the calculating portions 45a and 45b may create the information on the characteristic profiles, but the displaying portion 6 may create such information in place of the calculating portions 45a and 45b. The displaying portion 6 is capable of switching the kinds of pattern (e.g., the shape, the size, and the like of the pattern) to be displayed from one to another. In addition, the displaying portion 6 is capable of switching the characteristics to be displayed from the ones detected by the first characteristic-detecting portion 4a to the ones detected by the second characteristic-detecting portion 4b, or vice versa. Moreover, the displaying portion 6 can appropriately set the area to be displayed, the intensities in the profile, and the like.

The displaying portion 6 does not have to be provided in the characteristic-detection apparatus 1, but may be provided appropriately. For instance, the characteristic-detection apparatus 1 may be equipped with an unillustrated storage portion in place of the displaying portion 6. The storage portion stores, among other things, the data on the characteristics calculated by the calculating portions 45a and 45b.

Subsequently, the extracting portion 5 will be described furthermore.

Figure 2A:
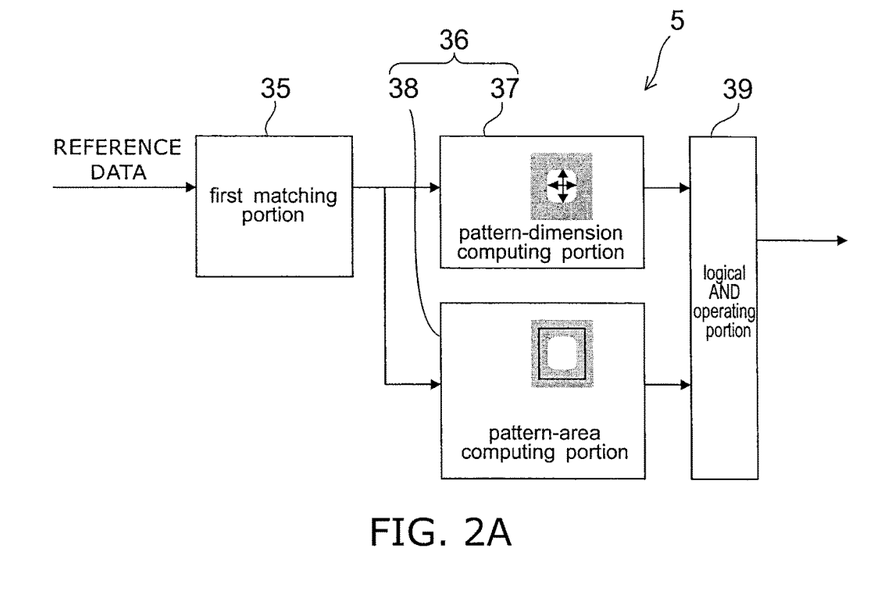
FIGS. 2A to 2G are schematic views for illustrating the extraction portion.
Figure 2B:
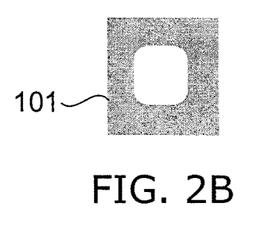
Figure 2C:
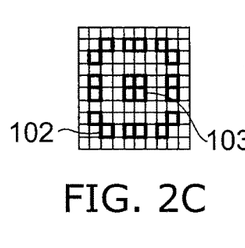
Figure 2D:
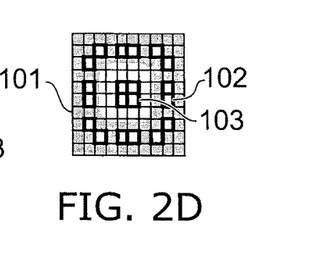
Figure 2E:
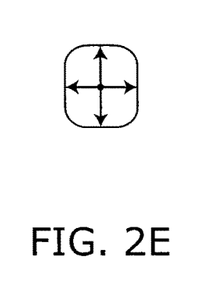
Figure 2F:
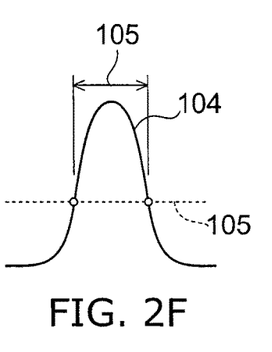
Figure 2G:
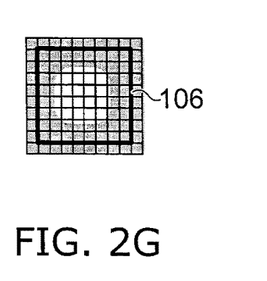

FIGS. 2A to 2G are schematic views for illustrating the extraction portion. FIG. 2A is a block diagram for illustrating the extraction portion. FIGS. 2B to 2D are schematic diagrams for illustrating how to carry out the template matching. FIG. 2E is a schematic diagram for illustrating the position where the pattern dimensions are detected. FIG. 2F is a schematic diagram for illustrating how to detect the pattern dimensions. FIG. 2G is a schematic diagram for illustrating how to carry out the matching based on the area of the pattern.

As FIG. 2A shows, the extracting portion 5 includes a first matching portion 35, a second matching portion 36, and a logical AND operating portion 39.

In this embodiment, the second matching portion 36 performs a pattern-matching operation on the pattern that is selected by the first matching portion 35. Accordingly, the target pattern can be extracted with higher accuracy.

The first matching portion 35 selects, from the reference data, a pattern with the same shape and size as those of the target pattern for the characteristic detection. The selection is carried out by performing a template-matching operation illustrated in FIGS. 2B to 2D. Specifically, a pattern 101 shown in FIG. 2B can be selected by performing a template-matching operation illustrated in FIG. 2D, using a template shown in FIG. 2C with thresholds 102 and 103. The threshold 102 is used when the target area for the matching has a smaller amount of transmitted light than a predetermined amount. The threshold 103 is used when the target area for the matching has a larger amount of transmitted light than a predetermined amount. The template shown in FIG. 2C is a fixed template in which the target area for the matching to be performed with the threshold 102 is located around the target area for the matching to be performed with the threshold 103.

The second matching portion 36 includes a pattern-dimension computing portion 37, and a pattern-area computing portion 38.

The pattern-dimension computing portion 37 performs a pattern-matching operation by computing dimensions of a pattern. For instance, the pattern-dimension computing portion 37 performs a pattern-matching operation by computing the pattern's dimensions in the directions that are normal to each other, as shown in FIG. 2E. In this case, as FIG. 2F shows, each of the pattern's dimensions can be computed on the basis of a profile 104 of the amount of transmitted light and a predetermined threshold 105. For instance, the dimension (denoted by reference numeral 105 in FIG. 2C) of the profile 104 at the threshold 105 can be defined as a pattern's dimension.

The pattern-area computing portion 38 performs a pattern-matching operation by computing the area of a pattern. For instance, as FIG. 2G shows, the pattern-area computing portion 38 performs a pattern-matching operation by computing the area, within a predetermined area 106, with a transmitted light's amount that is larger than a predetermined threshold. The above-mentioned area 106 is assumed to be an equivalent space to the target area for the matching performed with the threshold 102 and illustrated in FIG. 2C.

The logical AND operating portion 39 performs a logical AND operation on the matching results outputted from the pattern-dimension computing portion 37 and the pattern-area computing portion 38. The pattern extracted from the reference data in this way is a reference pattern with the same shape and size as those of the target pattern for the characteristic detection.

The template illustrated in FIG. 2C is a fixed template, but a variable template in which any matching area can be set as needed may be used in place of the fixed template. The extracting portion 5 may be equipped with a variable template in which any logic employed in each of the pixels included in the template can be set as needed.

Figure 3:
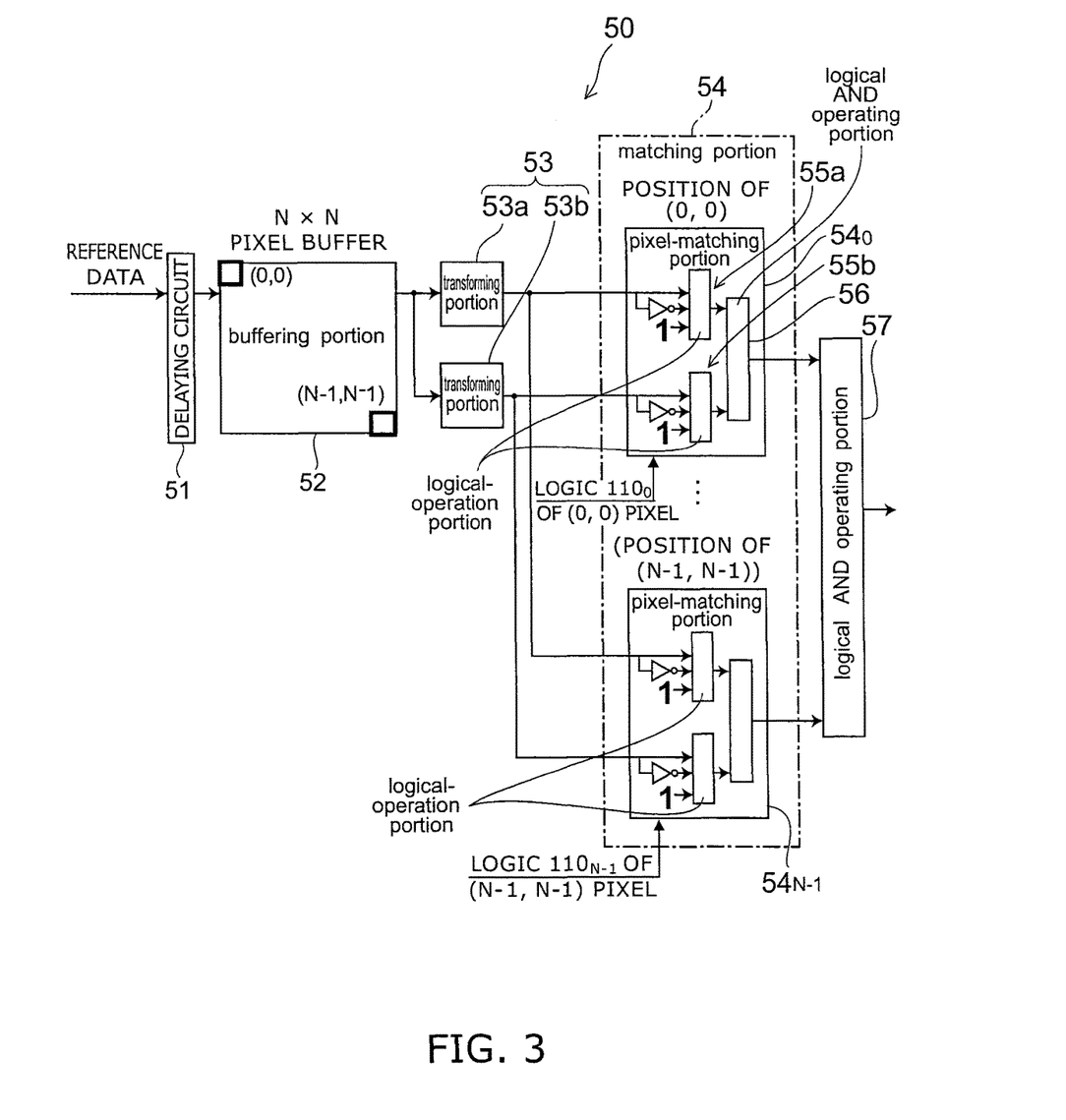
FIG. 3 is a block diagram for illustrating a variable template.

FIG. 3 is a block diagram for illustrating a variable template. To be more specific, the block diagram of FIG. 3 illustrates a variable template 50 included in the first matching portion 35. As FIG. 3 shows, the variable template 50 includes a delaying portion 51, a buffering portion 52, a binarizing portion 53, a matching portion 54, and a logical AND operating portion 57.

The delaying portion 51 delays, by a certain length of time, the transmission of the electric signal of the reference data without changing the waveform of the electric signal. The buffering portion 52 accumulates, as data of N×N pixels, the reference data inputted into the buffering portion 52 through the delaying portion 51.

The binarizing portion 53 includes transforming portions 53a and 53b. The transforming portions 53a and 53b perform binarization using different thresholds from each other. Some examples of the thresholds are the threshold 102 and the threshold 103.

The data of N×N pixels accumulated in the buffering portion 52 are binarized by the binarizing portion 53 using the different thresholds, and the binarized data are supplied to pixel-matching portions $54_0$ to $54_{N-1}$ each of which corresponds to a different group of N×N pixels. Note that the thresholds may be altered as needed.

The matching portion 54 includes the pixel-matching portions $54_0$ to $54_{N-1}$ each of which corresponds to a different group of N×N pixels. Each of the pixel-matching portions $54_0$ to $54_{N-1}$ includes logical-operation portions 55a and 55b, and a logical AND operating portion 56.

The logic employed by each of the logical-operation portions 55a and 55b can be set as needed. By allowing the logics in the logical-operation portions 55a and 55b to be set as needed, the template is formed as a variable template, in which the logic employed in each pixel in the template can be set as needed.

For instance, in the logical-operation portion 55a, one of the following three logics is selected and set: 'value of a particular pixel>threshold 103;' 'value of the particular pixel≤threshold 103;' and 'no computation is necessary.' In the logical-operation portion 55b, on the other hand, one of the following three logics is selected and set: 'value of a particular pixel>threshold 102;' 'value of the particular pixel≤threshold 102;' and 'no computation is necessary.' Determinations with the logics thus set are performed on the data provided by the binarizing portion 53.

The above-mentioned option 'no computation is necessary' can be selected and set when the value of the particular pixel is obvious. For instance, a pixel situated in a portion corresponding to a hole of a hole pattern (i.e., a light-penetrating portion) is obviously in a 'bright' state. In this case, by selecting and setting the value '1' shown in FIG. 3, the determination can be made that the pixel is 'ON (bright)' at all times.

The logical AND operating portion 56 performs a logical AND operation on the determination results outputted from the logical-operation portions 55a and 55b. The logical AND operating portion 56 thus outputs the result of matching for the particular pixel.

The logical AND operating portion 57 performs another logical AND operation on the result of the matching performed by the logical AND operating portion 56 in each of the p$54_0$ to $54_{N-1}$. If the matching is complete, the logical AND operating portion 57 outputs a 'template-matching result.' The 'template-matching result' is outputted to the area-setting portion 43 as a 'valid flag.'

Accordingly, it is possible to calculate the logical AND of the matching results of all the N×N pixels in accordance with the setting of logics of the template. Thus a template matching can be performed with the logics set as needed. If the template matching is performed with the logics set as needed, then a template more suitable for the shape or the like of the target pattern for the characteristic detection can be easily set based on a 'detection recipe' or the like.

Subsequently, detailed description will be given of the detection of characteristics (e.g., transmittance or the like) and the calculation performed on the characteristics.

Figure 4:
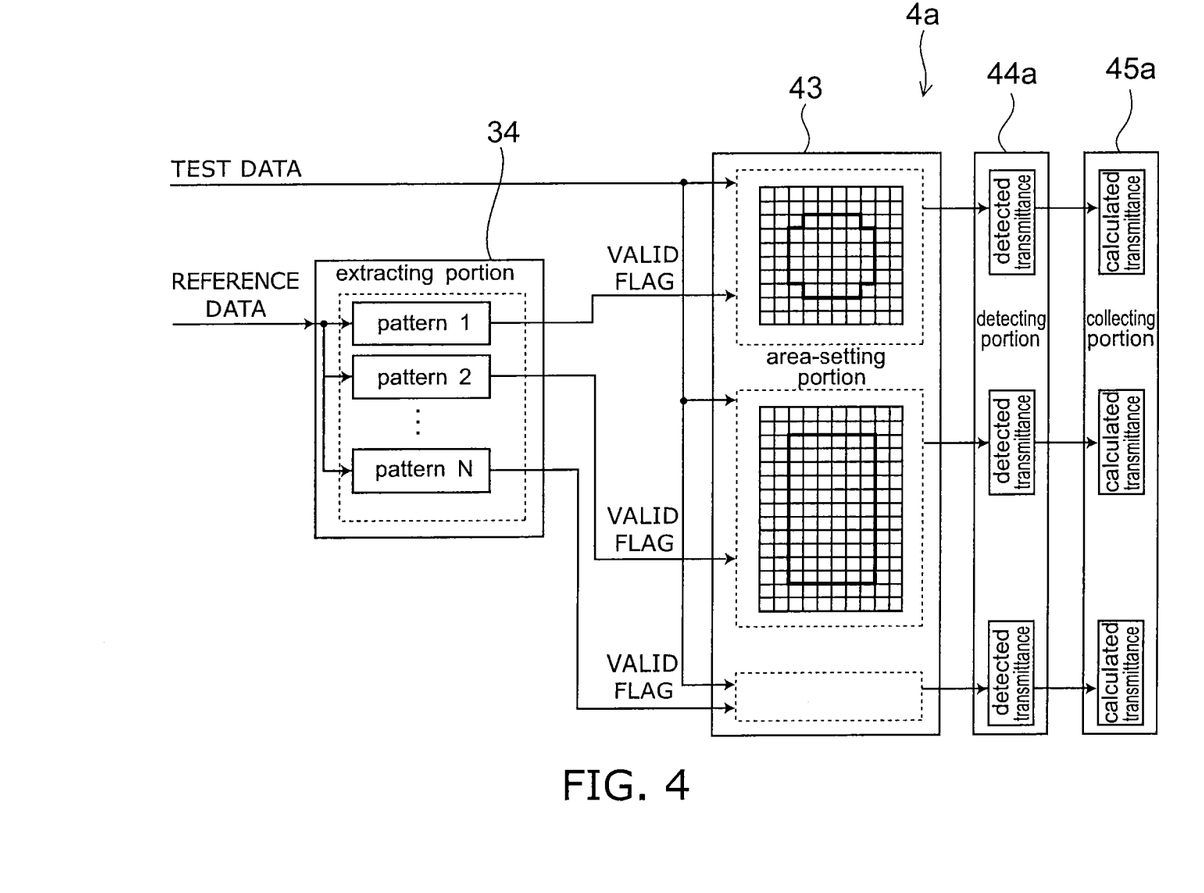
FIG. 4 is a block diagram for illustrating how to perform the detection of characteristics and the calculation on the characteristics.

FIG. 4 is a block diagram for illustrating how to perform the detection of characteristics and the calculation on the characteristics. Note that FIG. 4 shows an example of performing the detection of transmittance and the calculation on the transmittance.

As FIG. 4 shows, on the basis of the signal (valid flag) received from the extracting portion 5, the area-setting portion 43 sets an area as a target area where the transmittance of the pattern is to be detected. Here, on the basis of the signal (valid flag) received from the extracting portion 5, the area-setting portion 43 selects a template more suitable for the shape of the target pattern for the transmittance detection. In addition, on the basis of the positional information received from the extracting portion 5, the area-setting portion 43 extracts the target pattern for the transmittance detection from the detection data.

The detecting portion 44a detects the transmittance of the pattern on the basis of the area set by the area-setting portion 43 and the target pattern for the transmittance detection. For instance, the detecting portion 44a detects the transmittance of the pattern by calculating the sum of the data of the portion, within the set area, with values that are larger than a predetermined threshold.

The collecting portion 45a performs a calculation on the transmittance detected by the detecting portion 44a. The collecting portion 45a may be configured to calculate the transmittance for the entire area of the photomask. In addition, the collecting portion 45a may be configured to create information on the transmittance profile on the basis of the detected transmittance and the positional information.

Note that the description given by referring to FIG. 4 is based on the case of the first characteristic-detecting portion 4a. In the case of the second characteristic-detecting portion 4b, the detection of transmittance and the calculation on the detected transmittance may be performed in a similar manner.

In the case described so far, the area-setting portion 43 is equipped with a fixed template, but the area-setting portion 43 may be equipped with a variable template.

Figure 5:
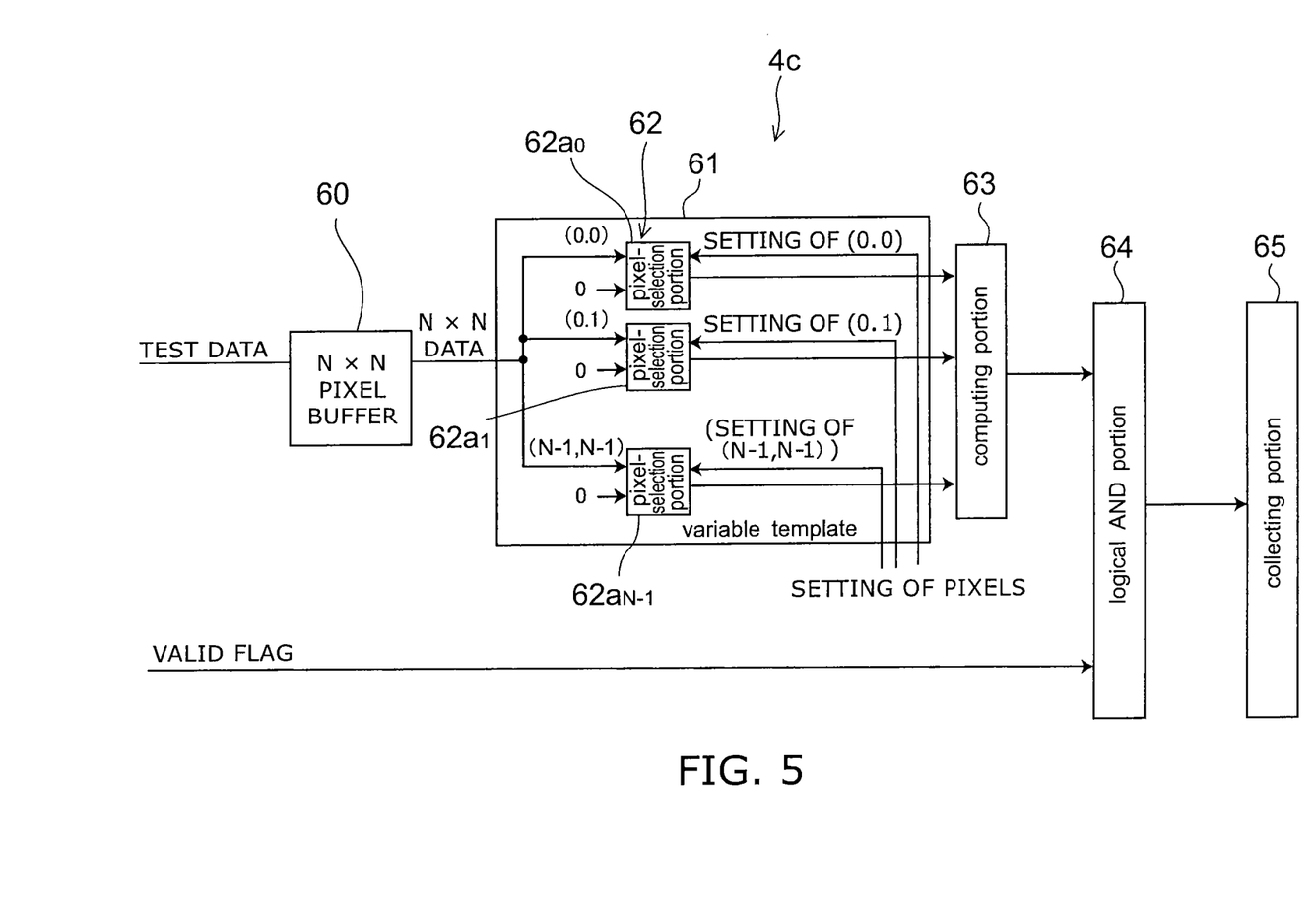
FIG. 5 is a block diagram for illustrating a case where a variable template is provided.

FIG. 5 is a block diagram for illustrating a case where a variable template is provided.

FIG. 5 shows a third characteristic-detecting portion 4c, which includes a buffering portion 60, a variable template 61, a computing portion 63, a logical AND portion 64, and an collecting portion 65.

The buffering portion 60 accumulates the inputted detection data as data of N×N pixels.

The variable template 61 includes a selecting portion 62. The selecting portion 62 includes pixel-selection portions $62a_0$ to $62a_{N-1}$, each of which corresponds to a different group of N×N pixels. In each of the pixel-selection portions $62a_0$ to $62a_{N-1}$, it is possible to set whether or not data on a particular pixel is to be selected (selection of pixel). By selecting certain pixels from the pixels included in the detection data, the selecting portion 62 can set a particular area as one where characteristics are to be detected. The computing portion 63 then computes the sum of the detection data within the set area.

The detection data are inputted, through the buffering portion 60 accumulating the data of N×N pixels, into the pixel-selection portions $62a_0$ to $62a_{N-1}$, each of which correspond to a different group of N×N pixels. The pixel-selection portions $62a_0$ to $62a_{N-1}$ are made to operate in accordance with the setting of whether or not a particular pixel is to be selected. Accordingly, the computing portion 63 can compute the sum of the values for the certain pixels thus set. In this way, it is possible to select pixels, as needed, as pixels set for the detection data and to computes the sum of the values of such selected pixels.

The logical AND portion 64 calculates the logical AND of the value of the total sum of the detection data computed by the computing portion 63 and the valid flag received from the extracting portion 5. In this way, it is possible to compute the total sum (characteristic value) in the target pattern, corresponding to the reference pattern, for the characteristic detection.

Accordingly, it is possible to calculate the total sum (characteristic value) of all the N×N pixels in accordance with the setting of logics of the variable template 61. Thus a characteristic detection can be performed with the logics set as needed. If the characteristic detection can be performed with the logics set as needed, then a template more suitable for the shape or the like of the target pattern for the characteristic detection can be easily set based on a 'detection recipe' or the like.

Subsequently, description will be given of the inverse-transformation operation and the computation of wafer plane pattern.

Figure 6:
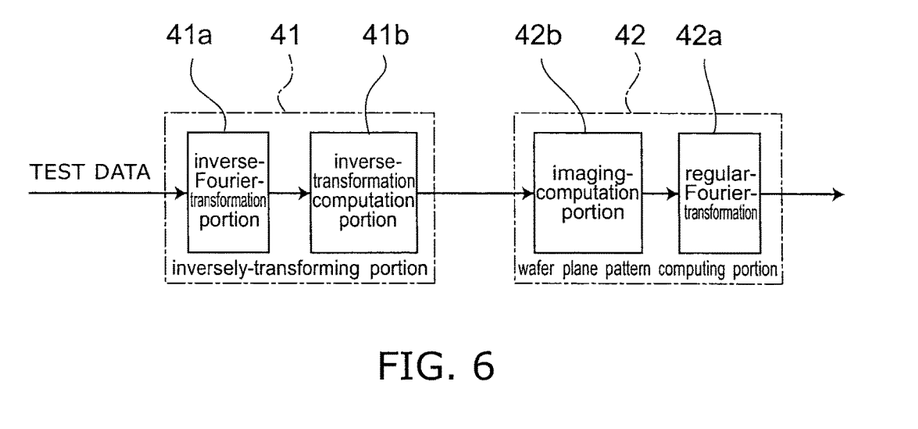
FIG. 6 is a block diagram for illustrating the inverse-transformation operation and the computation of wafer plane pattern.

FIG. 6 is a block diagram for illustrating the inverse-transformation operation and the computation of wafer plane pattern.

As FIG. 6 shows, the inversely-transforming portion 41 includes an inverse-Fourier-transformation portion 41a and an inverse-transformation computation portion 41b.

The inverse-Fourier-transformation portion 41a performs an inverse Fourier transformation on the detection data and transforms the detection data into the detection data on a Fourier plane.

The inverse-transformation computing portion 41b calculates, from the transformed detection data on the Fourier plane, the pattern formed on the photomask. To this end, the inverse-transformation computing portion 41b uses the optically-imaging characteristics of the imaging optical system 24 and the image-forming function—the one with the point spread function (PSF) taken into consideration—of the detecting portion 25.

The point spread function of the optical system (optically-imaging characteristics) and the image-forming function of the detecting portion 25 may be theoretically deduced on the basis of the optical properties and properties of the detecting portion 25 (e.g., so-called sensor properties or the like). Alternatively, the optically-imaging characteristics and the image-forming function may be determined experimentally or in other ways.

Detailed description will be given of how to calculate the pattern formed on the photomask from the detection data.

According to a theory on image formation, the output of the detecting portion 25 is expressed by Formula 1 given below. The output of the detecting portion 25 is obtained by firstly performing a convolution operation using the point spread function of the optical system (optically-imaging characteristics) and the image-forming function of the detecting portion 25, that is, the sensitivity profile of the individual pixels of the detecting portion 25. Following the convolution operation, sampling is performed using a comb function (comb) corresponding to the discrete sampling of the detecting portion 25.

[Numerical Expression 1]

$$i(x)=[d(x)*psf(x)*o(x)]\cdot comb(x) \quad (1)$$

In Formula 1, i(x) is the output of the detecting portion 25 (detection data), d(x) is the image-forming function of the detecting portion 25 (function of sensitivity profile of the sensor pixels), psf(x) is the point spread function of the optical system (optically-imaging characteristics), o(x) is the optical image obtained by the detecting portion 25, comb(x) is a function representing the positions (arrangement) of the pixels at a pitch p, and * represents a convolution operation.

By Fourier-transforming Formula 1, Formula 2 is obtained.

[Numerical Expression 2]

$$I(u)=D(u)OTF(u)O(u)*comb(u) \quad (2)$$

In Formula 2, I(u) is the Fourier-transformed output of the detecting portion 25 (detection data), D(u) is the Fourier-transformed image-forming function of the detecting portion 25 (function of sensitivity profile of the sensor pixels), OTF(u) is the Fourier-transformed point spread function of the optical system (optically-imaging characteristics), O(u) is the Fourier-transformed optical image obtained by the detecting portion 25, comb(u) is the Fourier-transformed function representing the positions (arrangement) of the pixels at a pitch p, and * represents a convolution operation.

Then, by inverse-Fourier-transforming Formula 2, Formula 3 is obtained. In this way, the pattern—the one on the Fourier plane—formed on the photomask can be calculated from the output signal of the detecting portion 25.

[Numerical Expression 3]

$$O(u)*comb(u)=I(u)/D(u)OTF(u) \qquad (3)$$

Note that in Fourier transformation such as one performed above, the bandwidth is limited by the pitch p of the pixels of the detecting portion 25. In this case, by performing zero-padding when the output of the detecting portion 25 (detection data) is Fourier-transformed, the band on Fourier plane can be widened.

Subsequently, the wafer plane pattern computing portion 42 will be described by referring back to FIG. 6.

The wafer plane pattern computing portion 42 includes a regular-Fourier-transformation portion 42a, and an imaging-computation portion 42b.

The imaging-computation portion 42b calculates the wafer plane pattern on the basis of the pattern calculated by the inverse-transformation computing portion 41b (i.e., the pattern formed on the photomask). Specifically, the wafer plane pattern on the Fourier plane is calculated by a printablity simulation. In the simulation, the light-source intensity profile of the exposure device, the pupil function of the optical system, the aberration property of the optical system, and the like are taken into consideration. The printablity simulation can be done using a known optical simulation tool for lithography and a computation hardware. Accordingly, no description will be given of the printablity simulation.

The regular-Fourier-transformation portion 42a Fourier-transforms the wafer plane pattern on the Fourier plane, and thus calculates the pattern (the wafer plane pattern in the real space) to be transferred onto the surface of the test sample 100.

Subsequently, the operation of the characteristic-detection apparatus 1 for photomasks and a method of detecting characteristics of photomasks will be described.

Firstly, an unillustrated conveying apparatus or an operator places the test sample 100 on the mounting portion 23. Then, the light source 21 emits the detecting light 21a. The detecting light 21a emitted from the light source 21 is guided by the illuminating optical system 22 to the detection area of the test sample 100, and the illuminating optical system 22 controls the size of the portion illuminated by the detecting light 21a. Then, the relative position within the test sample 100 placed on the mounting portion 23, where the characteristic detection is actually performed, is changed using an unillustrated unit for moving the test sample 100 or the like.

The detecting light 21a coming from the test sample 100 is guided by the imaging optical system 24 onto the light-receiving surface of the detecting portion 25, and form an image on the light-receiving surface. The light of the optical image formed on the light-receiving surface is converted by the detecting portion 25 into electricity. Then, the electric signal obtained by the light-electricity conversion performed by the detecting portion 25 is converted by the converting portion 26 into a digital signal. The converting portion 26 then graphically interprets the resultant digital electric signal to create detection data.

As the detection on the test sample 100 progresses, the data-storing portion 31 in the reference-data creating portion 3 supplies the design data or the like to the data-developing portion 32, where the supplied data are developed into two-dimensional data. The resultant two-dimensional data are graphically interpreted by the data-creating portion 33, and thus the reference data are created. Then, the extracting portion 5 extracts, from the reference data, a pattern (i.e., reference pattern) with the same shape and size as those of the target pattern for the characteristic detection. The extracting portion 5 outputs, to the area-setting portion 43, a signal (i.e., valid flag) about the extracted pattern. When outputting the above-mentioned signal, the extracting portion 5 also outputs the positional information of the extracted pattern, that is, the information on where in the photomask the extracted pattern is situated. The extraction of the reference pattern can be done using the fixed template, the variable template, or the like.

Then, the characteristic-detecting portion 4 detects characteristics of the target pattern for the detection, and performs collection, or the like, of the characteristics thus detected. On the basis of the signal (i.e., valid flag) received from the extracting portion 5, the area-setting portion 43 sets an area as the target area for detecting the characteristics of the pattern. In addition, on the basis of the positional information received also from the extracting portion 5, the area-setting portion 43 extracts, from the detection data, the target pattern for the characteristic detection.

Specifically, on the basis of the detection data, the first characteristic-detecting portion 4a detects characteristics of the target pattern for the detection, and performs collection, or the like, of the characteristics thus detected. In addition, the second characteristic-detecting portion 4b calculates, from the detection data, the wafer plane pattern. On the basis of the wafer plane pattern thus calculated, the second characteristic-detecting portion 4b detects the characteristics of the target pattern for the detection, and then performs collection or the like on the detected characteristics. The data on the characteristics thus collected or the like are visualized by the displaying portion 6. The displaying portion 6 may also display the characteristic profiles across the entire area of the photomask.

The method of detecting characteristics of a photomask according to the embodiment is carried out in the following way. On the basis of the optical image of the pattern formed on the test sample 100, the detection data are created. The reference data of the pattern formed on the test sample 100 are created. Both the reference pattern corresponding to the target pattern for the characteristic detection and the positional information of the reference pattern are extracted from the reference data. The area where the characteristics are to be detected is set on the basis of the reference pattern, and the target pattern for the characteristic detection is extracted from the detection data on the basis of the positional information. The characteristics of the target pattern for the characteristic detection within the target area for the characteristic detection are detected. The detected characteristics are collected.

Alternatively, on the basis of the optical image of the pattern formed on the test sample 100, the detection data are created. The reference data of the pattern formed on the test sample 100 are created. Both the reference pattern corresponding to the target pattern for the characteristic detection and the positional information of the reference pattern are extracted from the reference data. The pattern formed on the photomask is calculated from the detection data by performing an inverse-transformation operation. The wafer plane pattern is calculated from the pattern formed on the photomask. The area where the characteristics are to be detected is set on the basis of the reference pattern, and the target pattern for the characteristic detection is extracted from the wafer plane pattern on the basis of the positional information. The characteristics of the target pattern for the characteristic detection within the target area for the characteristic detection are detected. The detected characteristics are collected.

In addition, on the basis of the detected characteristics and the positional information, information on the characteristic profiles may be created.

The extraction of the reference pattern may be done using a variable template in which the logics employed in the pixels included in the template can be set as needed. In addition, the setting of the logics may be done on the basis of a 'detection recipe.'

In the description so far, the characteristics of the photomask is the transmittance, but characteristics of other kinds may be used. For instance, the line widths based on the line widths measurement may be performed in a similar manner to that in the case of the transmittance magnitude measurement. In addition, the transmittance magnitude in an area of the critical positions may also be detected. In addition, information on characteristic profiles of such other characteristics may be created. Accordingly, the user can have an idea on the characteristic profiles of other characteristics for the entire area of the photomask. In addition, some of the characteristics may be combined if necessary. Then the combined characteristics may be detected or collected. For instance, both the transmittance magnitude and the line width of the wafer plane image may be detected from the wafer plane pattern. Then, the transmittance profile and the line-width profile for the entire area of the photomask may be obtained by collection. In addition, the characteristic detection for photomasks may be combined with the testing of photomasks or the like. For instance, while the defects of a photomask are checked, the transmittance profile of a hole pattern, or the like, of special attention may be obtained for the entire area of the photomask. Accordingly, the user can recognize that there are anomalies that are not so critical as to be identified as defects. Consequently, the user can precisely evaluate the quality of the photomask, the cause of the lowering of the process margin attributable to the photomask and the like.

According to this embodiment, the characteristics (e.g., transmittance, line-width, etc.) and the characteristic profiles (e.g., transmittance profile, line-width profile, etc.) can be detected for the entire area of the photomask. If there are anomalies that are not so serious as to be regarded as defects, such anomalies may lower the process margin or the yield. Even in the cases where such problems occur, the causes of the problems can be identified accurately.

The photomask quality can be evaluated in terms of the uniformity, or the variation, of the transmittance or the line width, for example. In addition, evaluation of the process margin can be done in association with the photomask. Accordingly, it is possible to improve the yield in a lithography process.

In addition, the setting of the template, the setting of the parameters of the extracted pattern (e.g., parameters for the shape and size of the pattern), the setting of the area from which the transmittance or the line width is to be detected, or the setting of other kinds may be appropriately done with a 'detection recipe' or the like. In short, the template to be used in the extraction of the pattern or the like can be set as needed on the basis of the 'detection recipe' or the like.

Subsequently, another embodiment of the invention will be described below. This embodiment is applicable when the pattern formed on the photomask is calculated from the detection data.

Figure 7:
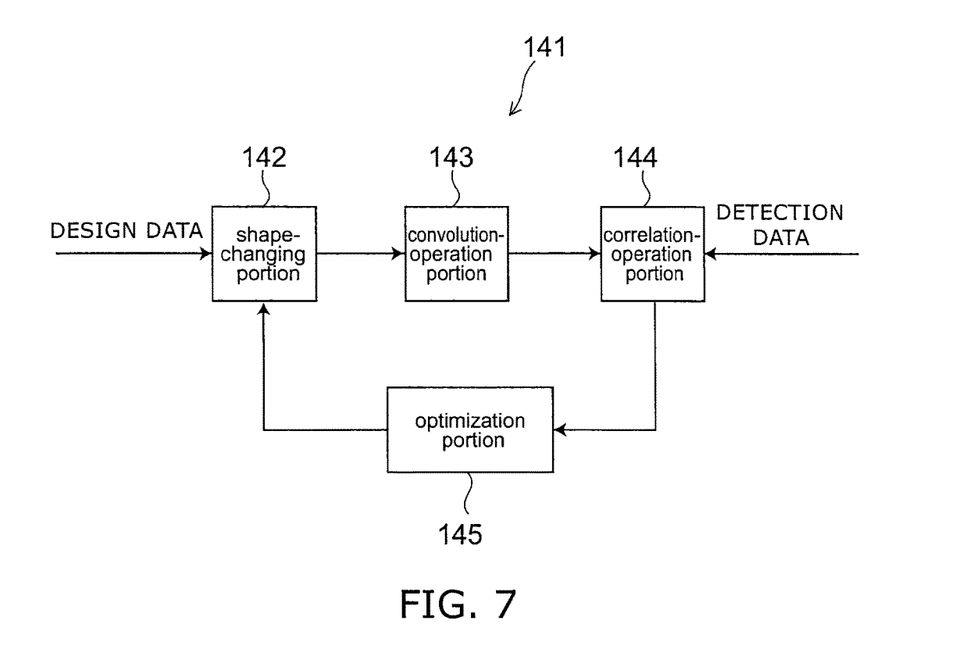
FIG. 7 is a block diagram for illustrating a transforming portion.

FIG. 7 is a block diagram for illustrating a transforming portion.

FIG. 7 shows a transforming portion 141, which includes a shape-changing portion 142, a convolution-operation portion 143, a correlation-operation portion 144, and an optimization portion 145.

The shape-changing portion 142 changes the shape and size of the pattern by changing the line-width value and/or the resizing parameter in a step-by-step manner.

The convolution-operation portion 143 performs a convolution operation using the point spread function (optically-imaging characteristics) of the optical system and the image-forming function representing the sensitivity profile of the pixels included in the detecting portion 25.

The correlation-operation portion 144 performs a correlation operation between the pattern data obtained by the convolution operation and the detection data.

The optimization portion 145 performs an optimization operation of the line-width value and/or the resizing parameter on the basis of the result of the correlation operation.

In the inversely-transforming portion 41 shown in FIG. 6, the detection data is transformed onto the Fourier plane by inverse Fourier transformation. From the transformed detection data on the Fourier plane, the pattern formed on the photomask is calculated using the optical-imaging characteristics and the image-forming function. According to this embodiment, on the other hand, a pattern that has the highest correlation with the detection data is calculated by a correlation operation, and the pattern thus calculated is identified as the pattern formed on the photomask.

For instance, the shape and size of the pattern in the design data inputted into the shape-changing portion 142 are changed by predetermined values, respectively. The convolution-operation portion 143 performs a convolution operation on the resultant pattern, and thus the pattern formed on the photomask is calculated. Then, a correlation operation is performed between the calculated pattern and the detection data. If the correlation is low, the optimization portion 145 performs optimization to increase the correlation. Then, the shape-changing portion 142 changes the line width and size of the pattern on the basis of the optimization data. Thereafter, the series of operations are repeated to identify a pattern correlating most with the detection data as the pattern formed on the photomask.

According to this embodiment, even if it is difficult to perform the inverse Fourier transformation, the pattern formed on the photomask can be calculated from the detection data. Accordingly, even if it is difficult to perform the inverse Fourier transformation, the characteristics concerning the wafer plane pattern can be detected.

In addition, not only for a contact-hole pattern and a particular line-and-space pattern, but also for the critical position in the pattern design, where the pattern is more likely to have defects, the transmittance magnitude in an area of the critical position can be measured and displayed in a similar manner.

Subsequently, a method of manufacturing a photomask according to this embodiment will be described.

According to the method of manufacturing a photomask according to this embodiment, the characteristic-detection apparatus 1 for photomasks and the method of detecting the characteristics of photomasks are used to calculate the characteristic profiles (e.g., transmittance profile, line-width profile, etc.) for the entire area of the photomask. The layout of the pattern (exposure-pattern data) is modified by taking the results of the characteristic detection. A photomask is fabricated on the basis of the modified pattern layout (exposure-pattern data). In this case, the photomask may be fabricated by etching.

Alternatively, information on the control of exposure conditions may be created instead of modifying the pattern layout (exposure-pattern data). For instance, information on the control may be created so that the exposure conditions can be changed in accordance with the characteristic profiles.

According to the method of manufacturing a photomask according to this embodiment, a photomask is obtained with uniform characteristic profiles for the entire area of the photomask. In addition, the user can recognize anomalies that are not so serious as to be regarded as defects. Accordingly, the quality of the photomask can be improved. In addition, the template to be used in the pattern extraction or the like can be set as needed on the basis of a 'detection recipe' or the like. Accordingly, improvements can be accomplished, for instance, in the yield, quality and productivity of photomasks. In addition, if information on the control of exposure conditions may be created so as to change the exposure conditions in accordance with the characteristic profiles, the yield of photomasks can be improved. In addition, improvements can be accomplished both in the quality and the yield of the product.

Subsequently, a method of manufacturing an electronic device according to this embodiment will be described.

In the following description, a method of manufacturing a semiconductor device is taken up as an example.

The method of manufacturing a semiconductor device is carried out by repeating plural processes. One of the plural processes is a process of forming a pattern on a wafer by film formation, resist application, exposure, development, etching, resist removal, and the like. Some of the other processes included in the above-mentioned plural processes are a testing process, a cleaning process, a heat-treatment process, an impurity-introduction process, a diffusing process, and a flattening process. In the manufacturing of semiconductor devices according to the method, a photomask with uniform characteristics is fabricated by the above-described method of manufacturing a photomask, and exposure is done using the photomask thus fabricated. In addition, the user can have a knowledge of the characteristic profiles for the entire area of the photomask before the exposure, the user can control, in accordance with the characteristic profiles, the exposure conditions in the exposure process. Here, the control can be performed on the basis of "the control information to change the exposure conditions in accordance with the characteristic profiles".

In the other processes than the one that employs the above-described method of manufacturing a photomask, the known techniques for the respective processes can be employed. Accordingly, no description will be given of such other processes.

The above-described method of manufacturing a semiconductor device is an example of the method of manufacturing an electronic device according to this embodiment. The method of manufacturing a semiconductor device, however, is not limited to this method. The method of manufacturing an electronic device of this embodiment can be widely employed in the electronic-device manufacturing using the photolithography technique. For instance, the method can be employed for the pattern formation in the manufacturing of flat-panel displays (e.g., the pattern formation on liquid-crystal color filters, array substrates and the like).

According to the method of manufacturing an electronic device according to this embodiment, a circuit pattern or the like is formed using a photomask with uniform characteristics. In addition, since the user can have a knowledge of the characteristic profiles for the entire area of the photomask before the exposure, the user can control, in accordance with the characteristic profiles, the exposure conditions in the exposure process. If a circuit pattern or the like deforms, various problems occur, such as degradation of the electric characteristics, the bridging of the circuit pattern, and the breaking of the circuit pattern. The control on the exposure conditions in accordance with the characteristic profiles can prevent such problems from occurring. Accordingly, improvements can be accomplished in the quality and yield of the product.

Some embodiments have been described so far, but the invention is not limited to these embodiments.

If those skilled in the art appropriately modify the above-described embodiments and as long as such modified examples have the characteristic features of the invention, the modified examples still remain in the scope of the invention.

For instance, the shape, the dimensions, the arrangement, the number, or the like of each of the elements included in the characteristic-detection apparatus 1 are not limited to the respective ones in the descriptions given so far, and can be changed if necessary.

In addition, the elements included in the above-described embodiments can be combined with one another if it is possible to do so. Examples with such combinations still remain within the scope of the invention as long as the characteristic features are included therein.

While certain embodiments have been described, these embodiments have been presented by way of example only, and are not intended to limit the scope of the inventions. Indeed, the novel devices and methods described herein may be embodied in a variety of other forms; furthermore, various omissions, substitutions and changes in the form of the devices and methods described herein may be made without departing from the spirit of the inventions. The accompanying claims and their equivalents are intended to cover such forms or modifications as would fall within the scope and spirit of the invention.

The invention claimed is:

1. A pattern characteristic detection apparatus for a photomask comprising:
　a detection-data creator configured to detect a pattern by converting light intensity of an optical image of the pattern formed on a photomask into an electric digital signal, the optical image of the pattern formed on a CCD image sensor, and to create detection data on the basis of the electric digital signal;
　a reference-data creator configured to create reference data of the pattern from design data of the pattern;
　an extractor configured to extract, from the reference data, the pattern with a same shape and size as those of a target pattern for pattern characteristic detection, and positional information of the extracted pattern;
　a characteristic-detector:
　　configured to set an area where pattern characteristics are to be detected on the basis of the extracted pattern, and configured to extract, from the detection data, the target pattern on the basis of the positional information of the extracted pattern;
　　configured to detect pattern characteristics of the target pattern for the pattern characteristic detection within the area where the pattern characteristics are to be detected; and
　　configured to collect the detected pattern characteristics;

the extractor including a variable matching template in which any matching logic based on the signal level of each pixel included in the template is settable as needed, the variable matching template executing a delaying, a buffering, a binarizing, and a plurality of pixel-matchings, the delaying delaying, by a certain length of time, a transmission of an electric signal of the reference data without changing a waveform of the electric signal, the buffering accumulating, as data of N×N pixels, the reference data inputted to be buffered after the delaying, the binarizing executing a first transforming and a second transforming, the first transforming and the second transforming performing binarization using different thresholds from each other, a data of N×N pixels accumulated in the buffering being binarized by the binarizing using the different thresholds, the binarized data being supplied to be subject to the plurality of pixel-matchings, each of the plurality of pixel-matchings corresponding to a different group of N×N pixels, each of the plurality of pixel-matchings executing a first logical-operation and a second logical-operation, the logic employed by each of the first logical-operation and the second logical-operation being set as needed, the characteristic-detector creating at least one of information on pattern characteristic distributions on the basis of the detected pattern characteristics and the positional information, and information on pattern characteristics for an entire area of the photomask.

2. The apparatus according to claim 1, wherein
the pattern characteristics are the characteristics of at least one kind selected from the group consisting of transmittance magnitude, a line width, and transmittance magnitude in an area of the critical position.

3. A pattern characteristic detection apparatus for a photomask comprising:
a detection-data creator configured to detect a pattern by converting light intensity of an optical image of the pattern formed on a photomask into an electric digital signal, the optical image of the pattern formed on a CCD image sensor, and to create detection data on the basis of the electric digital signal;
a reference-data creator configured to create reference data of the pattern from design data of the pattern;
an extractor configured to extract, from the reference data, the pattern with a same shape and size as those of a target pattern for pattern characteristic detection, and positional information of the extracted pattern;
an inverse-transformer configured to perform an inverse-transformation operation, from the detection data of a pattern formed on a photomask;
a wafer plane pattern computer configured to calculate a wafer plane pattern from the pattern formed on the photomask;
a characteristic-detector:
configured to set an area where pattern characteristics are to be detected on the basis of the extracted pattern, and configured to extract, from the wafer plane pattern, the target pattern on the basis of the positional information of the extracted pattern;
configured to detect pattern characteristics of the target pattern for the pattern characteristic detection within the area where the pattern characteristics are to be detected; and
configured to collect the detected pattern characteristics;
the extractor including a variable matching template in which any matching logic based on the signal level of each pixel included in the template is settable as needed, the variable matching template executing a delaying, a buffering, a binarizing, and a plurality of pixel-matchings, the delaying delaying, by a certain length of time, a transmission of an electric signal of the reference data without changing a waveform of the electric signal, the buffering accumulating, as data of N×N pixels, the reference data inputted to be buffered after the delaying, the binarizing executing a first transforming and a second transforming, the first transforming and the second transforming performing binarization using different thresholds from each other, a data of N×N pixels accumulated in the buffering being binarized by the binarizing using the different thresholds, the binarized data being supplied to be subject to the plurality of pixel matchings, each of the plurality of pixel matchings corresponding to a different group of N×N pixels, each of the plurality of pixel matchings executing a first logical-operation and a second logical-operation, the logic employed by each of the first logical-operation and the second logical-operation being set as needed, the characteristic-detector creating at least one of information on pattern characteristic distributions on the basis of the detected pattern characteristics and the positional information, and information on pattern characteristics for the entire area of the photomask.

4. The apparatus according to claim 3, wherein
the detection-data creator includes:
a light source configured to emit inspection light;
an illuminating optical system configured to guide the inspection light emitted from the light source to a photomask;
an imaging optical system configured to make inspection light from the photomask to form an optical image on a CCD image sensor of a detector; and
the characteristic-detector configured to convert light of the optical image formed on a CCD image sensor into electric digital signal, and
the inverse-transformation operation is performed using both an optically-imaging characteristic of the imaging optical system and an image-forming function representing sensitivity profile of pixels of CCD image sensor in the characteristic-detector.

5. The apparatus according to claim 3, wherein
the pattern characteristics are characteristics of at least one kind selected from the group consisting of transmittance magnitude, a line width, and transmittance magnitude in an area of the critical position.

* * * * *